(12) United States Patent
Zhang et al.

(10) Patent No.: US 10,950,378 B2
(45) Date of Patent: Mar. 16, 2021

(54) METHODS AND SYSTEMS FOR CONTROLLING ELECTROMAGNETIC FIELD GENERATORS

(71) Applicant: The Chinese University of Hong Kong, Hong Kong (CN)

(72) Inventors: Li Zhang, Hong Kong (CN); Lidong Yang, Hong Kong (CN); Edwin Yu, Kowloon (CN); Chi-Ian Vong, Macau (CN)

(73) Assignee: The Chinese University of Hong Kong, Hong Kong (CN)

( * ) Notice: Subject to any disclaimer, the term of this patent is extended or adjusted under 35 U.S.C. 154(b) by 175 days.

(21) Appl. No.: 16/358,524

(22) Filed: Mar. 19, 2019

(65) Prior Publication Data

US 2019/0295756 A1 Sep. 26, 2019

Related U.S. Application Data

(60) Provisional application No. 62/646,422, filed on Mar. 22, 2018.

(51) Int. Cl.
| | |
|---|---|
| *H01F 7/20* | (2006.01) |
| *H01F 7/06* | (2006.01) |
| *A61B 34/00* | (2016.01) |
| *A61B 17/00* | (2006.01) |
| *A61B 34/30* | (2016.01) |
| *A61B 17/70* | (2006.01) |

(52) U.S. Cl.
CPC ............. *H01F 7/064* (2013.01); *H01F 7/06* (2013.01); *H01F 7/20* (2013.01); *A61B 17/00* (2013.01); *A61B 17/7016* (2013.01); *A61B 34/30* (2016.02); *A61B 34/70* (2016.02)

(58) Field of Classification Search
USPC .................................................. 361/139, 143
See application file for complete search history.

(56) References Cited

U.S. PATENT DOCUMENTS

| | | |
|---|---|---|
| 4,674,481 A | 6/1987 | Boddie, Jr. et al. |
| 5,518,560 A | 5/1996 | Li |
| (Continued) | | |

FOREIGN PATENT DOCUMENTS

CN 202998534 U 6/2013

*Primary Examiner* — Danny Nguyen
(74) *Attorney, Agent, or Firm* — Kilpatrick Townsend & Stockton LLP (57) ABSTRACT

Disclosed are methods and apparatus for controlling electromagnetic field generation system to generate dynamic magnetic fields. The method can comprise: establishing a dynamic model that describes open-loop dynamics of the electromagnetic field generation system and has an unified state-space form with time delay; configuring a controller based on the dynamic model; applying, by the controller, a control signal to the electromagnetic field generation system; detecting one or more feedback signals from the electromagnetic field generation system; and updating, by the controller, the control signal for controlling the electromagnetic field generation system, according to a reference signal corresponding to a desired dynamic magnetic field, one or more compensated feedback signals, and system states. To address time delay and modeling error and to estimate system states, a Kalman filter and a Smith predictor based compensator can be incorporated.

29 Claims, 7 Drawing Sheets

(56) References Cited

U.S. PATENT DOCUMENTS

| | | |
|---|---|---|
| 5,908,444 A | 6/1999 | Azure |
| 6,353,763 B1 | 3/2002 | George et al. |
| 6,545,580 B2 | 4/2003 | Hegde et al. |
| 8,130,159 B2 | 3/2012 | Wuidart et al. |
| 2005/0205566 A1 | 9/2005 | Kassayan |
| 2008/0049372 A1 | 2/2008 | Loke |
| 2008/0284506 A1 | 11/2008 | Messer |
| 2015/0057676 A1* | 2/2015 | Muntwyler ............ A61B 34/70 606/130 |
| 2018/0067181 A1* | 3/2018 | Nogami ............... G01R 33/389 |

* cited by examiner

METHODS AND SYSTEMS FOR CONTROLLING ELECTROMAGNETIC FIELD GENERATORS

CROSS REFERENCE TO RELATED APPLICATIONS

This application claims the benefit of U.S. Provisional Patent Application No. 62/646,422, the disclosure of which is incorporated herein by reference.

TECHNICAL FIELD

This disclosure relates to electromagnetic field generation technology, in particular, to methods and systems for controlling an electromagnetic field generator to generate dynamic magnetic fields.

BACKGROUND

Recent studies have indicated the potential of using microscale (or nanoscale) robots (referred to collectively as "microrobots") in biomedicine applications, such as drug delivery, targeted therapy, and minimally invasive surgery. Among various techniques for actuating microrobots, magnetic field actuation has many advantages in the context of biomedicine. In particular, magnetic fields are considered harmless to living organisms and have the ability to penetrate deep tissues, allowing signals to be received. For magnetic actuation of microrobots, an electromagnetic coil system (ECS) is used to generate a real-time-controlled dynamic magnetic field. Many types of ECSs with different coils, coil driving modules and control systems have been developed to manipulate microscale and nanoscale devices. In addition, in magnetic particle imaging, ECSs are also used for dynamic imaging magnetic particle tracers.

Magnetic microrobots have various motion principles, and their working frequencies can exceed 100 Hz, making ECS particularly useful for generating dynamic fields for actuation of magnetic microrobots. For example, an ECS can be operated to generate rotating magnetic fields for actuating helical microrobots and nanoparticle swarms, oscillating magnetic fields for actuating micro-robots with elastic tails or with a flexible link, conical magnetic field for actuation of nanowires, square magnetic fields for actuation of resonant magnetic microrobots, and so on. Therefore, the accuracy of dynamic magnetic fields generated by an ECS is essential for high-precision motion control of microrobots and characterization of microrobot behavior.

To control the dynamic magnetic fields in an ECS, the current(s) passing through coil(s) for the ECS need to be regulated. Two types of coil driving modules are typically used to drive electromagnetic coils with dynamically changing currents. One type uses commercially-available servo-amplifiers, which can linearly convert an input voltage (representing a command) to an electric current output to the coils. This approach can simplify the driving system, and an open-loop control structure is usually adopted. Another type of coil driving module uses a power inverter-based circuit board to control the dynamic voltage applied on the coil, usually in combination with simple proportional-integral (PI) control. This approach supports higher control frequency, but the relatively complex control implementation adds to development time and cost. In addition, for either type of systems with open-loop control, due to the influence of coil inductance on the dynamics of the coil driving system, the output magnetic field may diverge from the input command when high-frequency magnetic fields are being generated. Therefore, it can be beneficial to introduce closed-loop control (e.g. proportional-integral-derivative (PID) control or model-based control) into ECSs to allow more precise behavioral study and motion control of magnetic microrobots.

However, applying conventional closed-loop control methods to ECSs presents many difficulties. For example, conventional PID controllers are sensitive to system uncertainties (e.g. variation of the coil resistance) and external disturbances (e.g. mutual inductance) because they ignore the system dynamics. Besides, PID control usually has large overshoot and settling time, and magnitudes of PID gains are limited when there is feedback noise. An alternative to PID control is model-based control. However, model-based control of ECSs is challenging since the dynamic model of the servoamplifier and coil cannot be established directly and since different driving system configurations have diverse dynamics, which make it difficult to represent different ECSs using a unified model. Furthermore, the model should consider system time delays and noise in order to avoid large overshoot and system chattering, which makes the optimal control problem even more difficult.

SUMMARY

The present disclosure provides examples (also referred to as "embodiments") of electromagnetic coil systems for generating dynamic magnetic fields with high accuracy. These examples include specific detail to facilitate understanding; however those skilled in the art with access to this disclosure will appreciate that the claimed invention can be practiced without these details.

Some embodiments described herein relate to a method for controlling electromagnetic field generation system to generate dynamic magnetic fields. The method may comprise: establishing a dynamic model describing open-loop dynamics of the electromagnetic field generation system that has an unified state-space form with time delay; configuring, e.g., by linear quadratic with integral action (LQI) technique, a controller based on the dynamic model; applying, by the controller, an initial control signal to the electromagnetic field generation system; detecting one or more feedback signals from the electromagnetic field generation system, wherein the one or more feedback signals are generated in response to the control signal; and updating, by the controller, the control signal for controlling the electromagnetic field generation system, according to a reference signal corresponding to a desired dynamic magnetic field, the one or more feedback signals and system states of the electromagnetic field generation system. The feedback signal may include any signal or combination of signals containing information about the condition of the electromagnetic field, including but not limited to electric current, magnetic flux density or displacement, or any combination of electric current, magnetic flux density and displacement.

According to some embodiments described herein, the electromagnetic field generation system comprises at least one pair of load driving module and connected load, the dynamic model comprises at least one state-space model with unified state-space form, and the state-space model describes open-loop dynamics of one pair of load driving module and connected load in the electromagnetic field generation system. The load may be one or more wire sections in any shape, such as straight, circular, rectangular or coiled, and may be connected in series or parallel. In some embodiments, the load driving module may be a coil driving module, the connected load may be a coil connected to the coil driving module, and the electromagnetic field generation system may be an electromagnetic coil system (ECS).

According to some embodiments described herein, configuring the controller further comprises: fitting a p-dimensional minimum-phase state-space model with experimental open-loop frequency response data of sensor feedback (such as electric current) of the electromagnetic field generation system; identifying the time delay of the fitted model by an experimental open-loop step response in time domain of the electromagnetic field generation system; and configuring the controller based on the identified model, by linear quadratic with integral action (LQI) technique.

According to some embodiments described herein, the generating further comprises: transforming the identified model from a continuous-time system model into a discrete-time system model by zero-order hold (ZOH) method.

According to some embodiments described herein, the electromagnetic field generation system may be an ECS. The ECS may be a multi-axis system having a coil driving module and corresponding coil for each axis. In some embodiments, the electromagnetic field generation system may be a multi-axis system having a load driving module and corresponding connected load for each axis. The connected load for an axis can be, for example, one or more wire sections in any shape, and wire sections may be connected in series or parallel.

According to some embodiments described herein, a feedback signal may include or be based on a reading containing magnitude information of electric current, magnetic flux density, or any other measurable electromagnetic field condition.

According to some embodiments described herein, for each pair of load driving module and connected load, configuring the controller further comprises: adding an integral action augmented state into the state-space model to form an augmented system model to minimize tracking error during control, wherein the integral action augmented state describes an integral action of an error of the magnetic field generated by the pair of load driving module and connected load; and configuring the controller based on the augmented system model.

According to some embodiments described herein, configuring the controller further comprises: providing the augmented system model with a weighting matrix for penalizing states of the augmented system model and a control weighting parameter for penalizing a control effort; determining the weighting matrix and the control weighting parameter to minimize a cost function based on LQI technique for optimizing the transient response of the electromagnetic field generation system; and configuring the controller based on the weighting matrix and the control weighting parameter.

According to some embodiments described herein, the weighting matrix comprises a weighting element for penalizing the integral action augmented state.

According to some embodiments described herein, the weighting matrix is configured to penalize the states of the augmented system model for optimal system performance, such as avoiding excessive voltage spike due to high inductance load in system, which can be adjusted to adapt to different properties of a particular ECS.

According to some embodiments described herein, a control weighting parameter is configured to penalize the control effort for optimal system performance, such as avoiding controller saturation, which can be adjusted to adapt to different driving capabilities of a particular ECS.

According to some embodiments described herein, detecting the one or more feedback signals comprises: storing the control signal in real time; measuring a feedback signal indicative of an electromagnetic field condition (which may include one or more such conditions) of the electromagnetic field generation system in real-time; estimating a noise-free past system state and at least one noise-free past feedback signals based on the measured feedback signal and the stored control signal; predicting, based on the dynamic model, a present system state, a past system state, a present feedback signal, and a past feedback signal; compensating the predicted present system state based on the difference between the predicted past system state and the estimated noise-free past system state, and compensating the predicted present feedback signal based on the difference between the predicted past feedback signal and the estimated noise-free past feedback signal; and outputting the compensated predicted present system state and the compensated predicted present feedback signal to the controller. The controller can update the control signal based on the compensated predicted present feedback signal, the compensated predicted present system state, and the reference signal corresponding to a desired dynamic magnetic field. In some embodiments, the system state can be represented as a state vector, which may be p-dimensional. The number of dimensions p can be fitted from the open-loop frequency magnitude response at the fitting step and is independent of the feedback signals.

According to some embodiments described herein, the estimating can be implemented by a Kalman filter based on experimental open-loop step response data.

According to some embodiments described herein, the predicting can be implemented by a Smith Predictor.

Some embodiments described herein relate to an apparatus for controlling electromagnetic field generation system to generate dynamic magnetic fields. The apparatus may comprise: a controller configured to apply a control signal to the electromagnetic field generation system; and a detector configured to measure an electromagnetic field condition of the electromagnetic filed generation system and to generate one or more feedback signals, wherein the one or more feedback signals are generated in response to the control signal and the measured electromagnetic field condition; wherein the controller is further configured to update the control signal for controlling the electromagnetic field generation system based in part on a reference signal corresponding to a desired dynamic magnetic field of the electromagnetic field generation system, in part on the one or more feedback signals, and in part on one or more system states; and wherein the controller is further configured to update the control signal based on a dynamic model for describing open-loop dynamics of the electromagnetic field generation system that has an unified state-space form with time delay.

The following detailed description, together with the accompanying drawings, will provide a better understanding of the nature and advantages of the claimed invention.

DETAILED DESCRIPTION

Specific examples (also referred to as "embodiments") of control systems and electromagnetic field generation systems for generating dynamic magnetic fields with high accuracy are described herein. These examples include specific detail to facilitate understanding; however those skilled in the art with access to this disclosure will appreciate that the claimed invention can be practiced without these details. It should also be understood that features and details described with respect to different embodiments can be used in combination except in instances where logic dictates otherwise.

Figure 1:
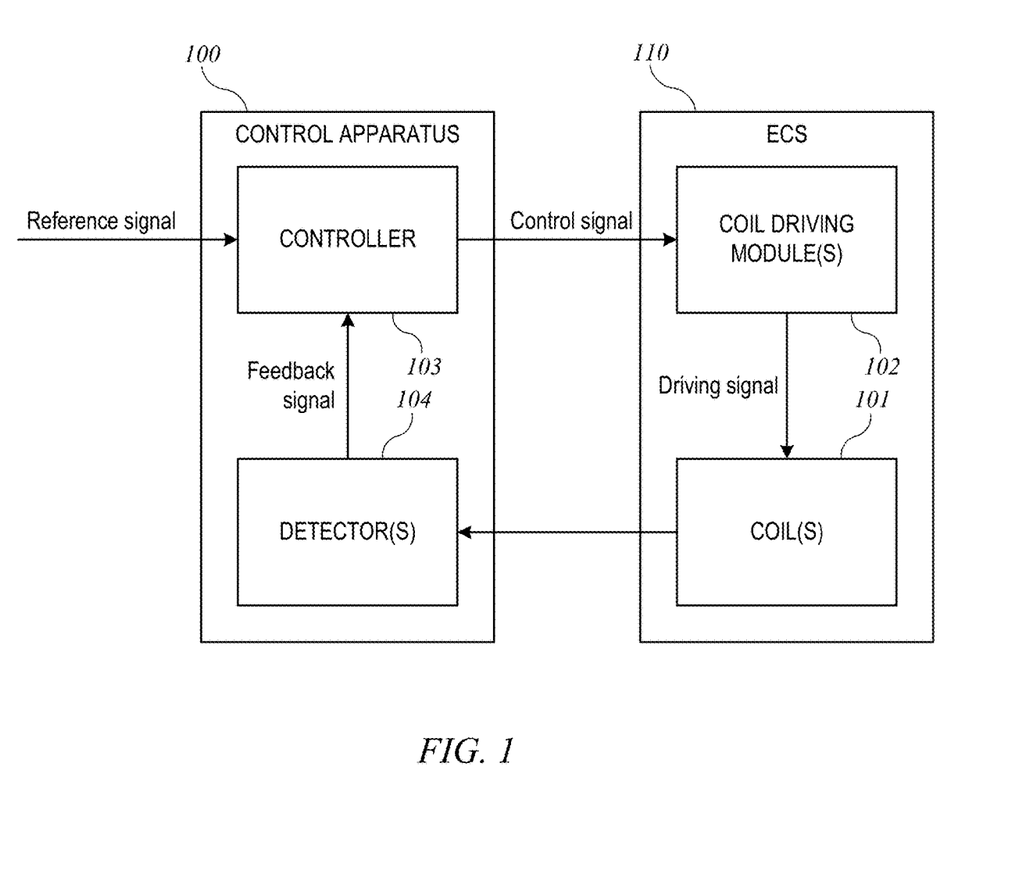
FIG. 1 shows a block diagram of an apparatus for controlling an electromagnetic coil system (ECS) to generate dynamic magnetic fields according to some embodiments.

FIG. 1 shows a block diagram of an apparatus 100 for controlling an electromagnetic coil system (ECS) 110 to generate dynamic magnetic fields according to an embodiment. As shown in FIG. 1, ECS 110 may include one or more electromagnetic coils 101 operable to generate dynamic magnetic fields and one or more coil driving modules 102 operable to produce dynamic electric currents in electromagnetic coils 101. In some embodiments, electromagnetic coils 101 can be coils of conductive wire (e.g., copper wire); other shapes may also be used. It is assumed that changing a current passing through electromagnetic coils 101 results in generating a magnetic field, which can be dynamically controlled by controlling the current. Coil driving modules 102 can include circuitry to generate a current in response to a control signal such that the amount of current is based on (e.g., proportional to) the control signal; numerous examples of such circuitry are known in the art.

Control apparatus 100 includes a digital controller 103 configured to calculate control signals for coil driving modules 102 and a detector 104 to generate feedback signals, e.g., based on detected electromagnetic field conditions. Digital controller 103 can include a logic circuit (e.g., a microprocessor or microcontroller) configured with control logic to determine a desired current in response to a desired magnetic field profile, which can be specified using a reference signal input to digital controller 103. In some embodiments, the reference signal can be generated in real time and may indicate the desired magnetic field strength (e.g., magnetic flux density). In other embodiments, the reference signal can be provided in advance of system operation (e.g., as a script specifying desired magnetic field strength as a function of time) and stored by digital controller 103 for subsequent operation. Regardless of the format of the reference signal, the logic circuits of digital controller 103 can be configured to determine a desired current for the coils based on the desired magnetic field (or other information in the reference signal) and based on a feedback signal from detector 104. In some embodiments, digital controller 103 can include additional logic circuitry and/or program code to establish a dynamic model describing open-loop dynamics of ECS 110, e.g., based on measuring an open-loop step response of ECS 110. Specific examples of configuration and operation of controller 103 are described below.

Detector 104 can include one or more sensors that sense a condition related to the electromagnetic field generated in ECS 110. Examples of appropriate sensors include a current sensor to sense the actual current in coils 101, a magnetic flux density sensor to measure the magnetic flux density, a displacement sensor to detect displacement, and so on. Detector 104 can also include control logic or other circuitry (e.g., analog-to-digital converters) to generate one or more feedback signals (which can be digital signals) based on the sensed electromagnetic field condition(s). Specific examples of control logic are described below.

In operation, controller 103 can receive a reference signal indicating a desired magnetic field strength. Based on the reference signal, controller 103 can generate (e.g., in real time) a series of control signals to coil driving module 102. In response to the control signals, coil driving module 102 can generate driving signals to produce coil currents in electromagnetic coil 101. The coil currents induce a magnetic field. Detector 104 can operate its sensors to detect an electromagnetic field condition and can generate a feedback signal to controller 103. Based on the feedback signal and the reference signal, controller 103 can modify the control signals to continue to produce the desired dynamic magnetic field.

Controller 103 may use various feedback algorithms to modify control signals based on the feedback signal and the reference signal. In some embodiments, modified control signals can be generated based on a dynamic model by linear quadratic integral (LQI) technique, using a dynamic model that describes open-loop dynamics of ECS 110 and that has an unified state-space form with time delay. The unified state-space form may describe different driving system configurations having diverse dynamics, which makes it easy to apply the same controller 103 to diverse instances of ECS 110 with diverse dynamics.

It will be appreciated that the system shown in FIG. 1 is illustrative and variations and modifications are possible. For instance, the electromagnetic coil system may be replaced by another type of electromagnetic field generation system. Thus, for example, coil 101 can be replaced more generally by an electrical load (e.g., one or more wire sections in any shape, including but not limited to rectangular, circular, or coiled shapes, with multiple wire sections connected in series or parallel), and coil driving module(s) 102 can be replaced more generally by a load driving module. Regardless of the particular implementation of the electromagnetic field generating system, controller 103 can use a dynamic model that includes at least one state-space model with unified state-space form, where the state-space model describes open-loop dynamics of one pair of load driving module and connected load in the electromagnetic field generation system.

It should also be noted that generation of the feedback signal is not limited to an electric current signal but may include any single reading or combinations of readings containing system-related information, including but not limited to electric current, magnetic flux density or displacement, or any combination of electric current, magnetic flux density and displacement, or any other measurable characteristic indicative of an electromagnetic field condition.

In some embodiments, ECS 110 may be a 3-axis Helmholtz coil system comprising a separate coil and coil driving module for each axis. Controller 103 maybe a model-based controller that generates a control signal for each axis. Controller 103 can model each axis of ECS 110 using a simple process of parameter tuning (described below). Thus, controller 103 can be used to control combinations of coils having different parameters, which may be required in some instances (e.g., to actuate microrobots in multiple degrees of freedom).

For purposes of description, two example ECSs with 3-axis Helmholtz coils are chosen to illustrate features of a model-based controller. However, the ECS is not limited to 3-axis Helmholtz coil systems, and other multi-axis (or single-axis) coil systems may be used.

In order to investigate parameter tuning for different coils, lab-constructed 3-axis Helmholtz coils have been utilized in two ECSs. There are significant differences in resistances and inductances of the three coil axes, indicating their diverse dynamics. The field strength b(t) at the center area of a Helmholtz coil axis excited by a dynamic electric current I(t) can be calculated by:

$$b(t)=\alpha I(t), \quad (1)$$

where the constant $\alpha$ for each coil axis can be calibrated using a Gaussmeter. In one example, $\alpha=3.5$ mT/A. Accordingly, in some embodiments magnetic field strength can be measured by electric current sensors because of the linear relationship between the magnetic field strength and electric current in the coil. (It is noted that the linear relationship still holds for a coil with iron core.) A linear relationship as in Eq. (1) is not required, and in some embodiments magnetic field strength b(t) can be measured directly rather than inferring b(t) from I(t).

A first example ECS (referred to for convenience as "ECS-I") has a computer-based control system with servo-amplifiers for driving the coils. The relationship between a constant voltage input $u_1$ and the steady state current output I of the servoamplifier is $$I=c_1 u_1, \quad (2)$$

where $c_1$ is a constant that depends on the particular servo-amplifier. In the present example, $c_1=1$. For feedback of the generated magnetic field, electric current sensors integrated in the servoamplifiers collect the coil current signals, which are then converted from analog to digital using an analog/digital converter (ADC). A power supply provides power for the servoamplifiers. An oscilloscope is used to record the measured coil currents and control inputs in real time.

A second example ECS (referred to as "ECS-II") has an embedded control system with custom-designed circuit board for driving the coils. The driving circuit can include switching regulators (e.g., bipolar junction transistors and/or field effect transistors) with accessory circuits to power the regulators, thereby producing current pulses of a desired duration, frequency, or shape, allowing pulse width modulation (PWM) techniques to be used to provide controllable power to the coils. The effective control voltage V(t) exerted on the coil can be approximated as:

$$V(t) = \frac{c_2}{MaxCount} V_{DC} u_2(t) = \beta u_2(t), \quad (3)$$

where MaxCount stands for the count value of the PWM when the duty cycle of the inverter equals to 100%. $V_{DC}$ and $u_2(t)$ are the voltage of the power supply and computed input command of the controller, respectively. Coefficient $c_2$ is calibrated for a specific coil such that an unitary input causes an unitary current output in the coil at the steady state. As a result, $\beta$ is a constant associated with a specific coil. For coil current feedback, current sensors integrated on the circuit boards are used.

In some embodiments, the three pairs of coils and coil driving module can be considered as three independent systems since mutual inductance between any two of the coil axes is negligible. The mathematical model of the dynamics of servoamplifiers in ECS-I cannot be established directly; however, it can be approximated using a p-dimensional state-space model through system identification. As shown below, p is identified as 1 and 2 for ECS-II and ECS-I, respectively.

Figure 2:
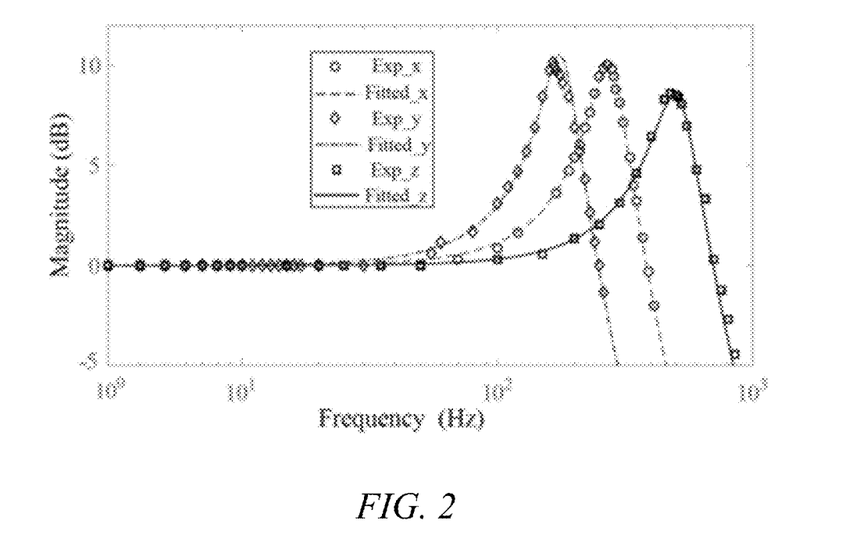
FIG. 2 shows Bode diagrams of measured open-loop frequency magnitude responses and fitted models for a first electromagnetic coil system (ECS-I).
Figure 3:
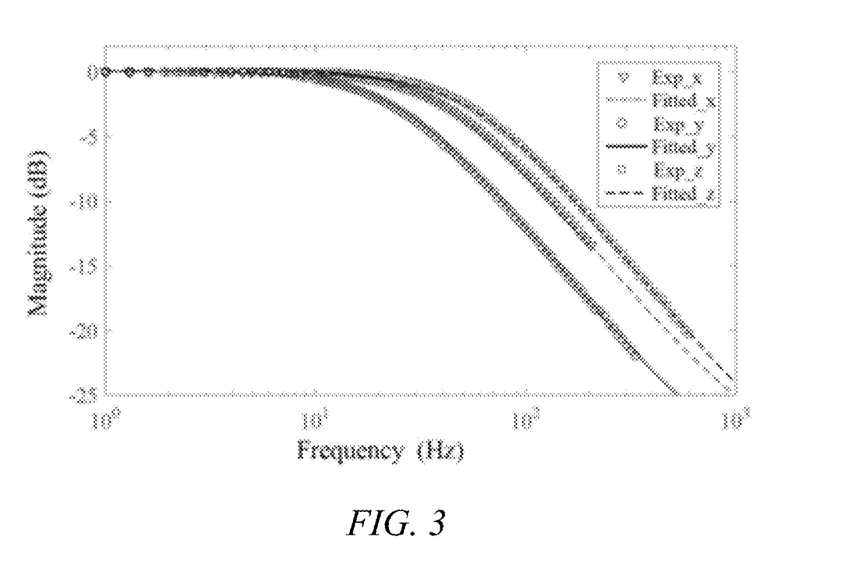
FIG. 3 shows Bode diagrams of measured open-loop frequency magnitude responses and fitted models for a second electromagnetic coil system (ECS-II).
Figure 4:
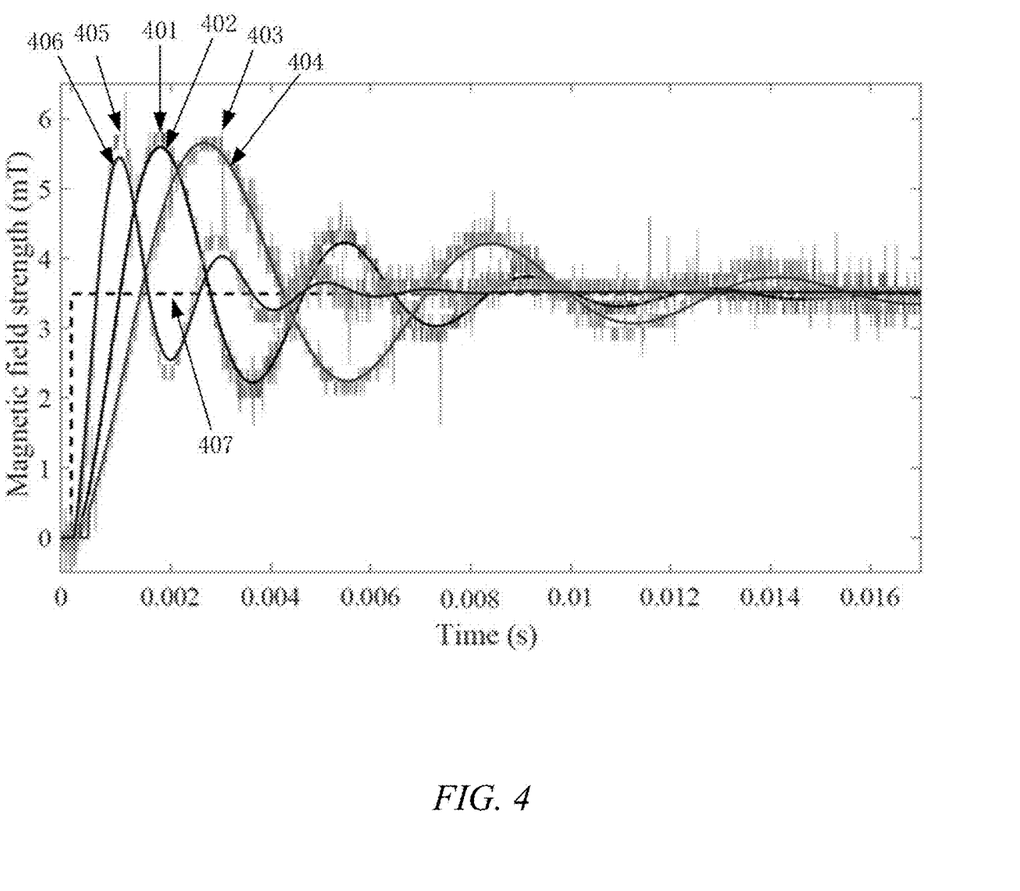
FIG. 4 shows comparisons of the open-loop step responses between the identified time-delayed models and the experimental data for ECS-I.
Figure 5:
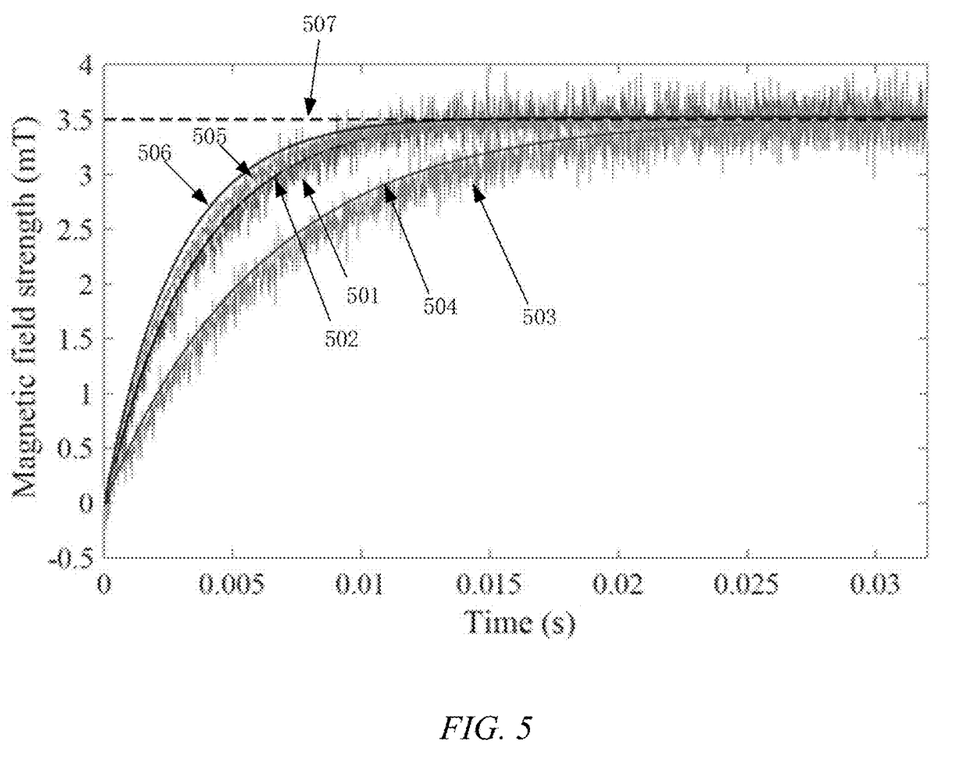
FIG. 5 shows comparisons of the open-loop step responses between the identified time-delayed models and the experimental data for ECS-II.

To identify the dynamics of each pair of coil 101 and coil driving module 102 in the two ECSs, controller 103 delivers sinusoidal control signals (disregarding any feedback signal from detector 104) to the coil driving modules 102 of the three axes, and the signals indicating the coil currents are measured by the corresponding detector 104. The resulting open-loop frequency magnitude response of ECS-I and ECS-II is plotted as FIG. 2 and FIG. 3, respectively. Specifically, FIG. 2 shows the Bode diagrams of the open-loop frequency magnitude responses and fitted models for each axis of ECS-I, and FIG. 3 shows the Bode diagrams of the open-loop frequency magnitude responses and fitted models for each axis of ECS-II. From the data, it can be concluded that dynamics of each pair of coil driving module and coil in ECS-I and ECS-II can be modeled as a second order and a first order system, respectively. Since time delay does not affect the frequency magnitude response, delay-free dynamic models can be obtained by fitting the data with p-dimensional (for example, p=2 for ECS-I, and p=1 for ECS-II) minimum-phase state-space models using a log Chebyshev magnitude approximation algorithm. The fitted results are also displayed in FIG. 2 and FIG. 3. Furthermore, time delays are identified by experimental data of the time domain step responses illustrated in FIG. 4 and FIG. 5. Specifically, FIG. 4 shows comparisons of the open-loop step responses between the identified time-delayed models and the experimental data for ECS-I, where curve 401 represents the experimental data of X axis, curve 402 represents the identified (model) data of X axis, curve 403 represents the experimental data of Y axis, curve 404 represents the identified (model) data of Y axis, curve 405 represents the experimental data of Z axis, curve 406 represents the identified (model) data of Z axis, and dotted line 407 represents the reference signal. FIG. 5 shows comparisons of the open-loop step responses between the identified time-delayed models and the experimental data for ECS-II, where curve 501 represents the experimental data of X axis, curve 502 represents the identified (model) data of X axis, curve 503 represents the experimental data of Y axis, curve 504 represents the identified (model) data of Y axis, curve 505 represents the experimental data of Z axis, curve 506 represents the identified (model) data of Z axis, and dotted line 507 represents the reference signal.

From FIG. 4 and FIG. 5, it can be observed that the fitted models with time delays have good agreement with the experimental data; thus, the models can be used to represent the system dynamics. The identified state-space dynamic model with a unified form for the two developed electromagnetic coil systems may be represented by:

$$\begin{cases} X_j(t) = A_j X_j(t) + B_j u_j(t - L_j) \\ I_j(t) = C_j X_j(t) + D_j u_j(t - L_j) \end{cases}, j = x, y, z \quad (4)$$

where the subscript j indicates the coil axis (x, y or z); $u_x$, $u_y$ and $u_z$ are the corresponding control inputs of three coil axes, which are time-delayed by $L_x$, $L_y$ and $L_z$, respectively; and $I_x$, $I_y$ and $I_z$ are the corresponding currents of the three coil axes. The identified parameters of $A_{x,y,z} \in R^{p \times p}$, $B_{x,y,z} \in R^{p \times 1}$, $C_{x,y,z} \in R^{1 \times p}$, $D_{x,y,z} \in R^{1 \times 1}$. By Eq. (1), the generated dynamic magnetic field $b_j(t)$ (unit: mT) may be calculated by:

$$b_j(t) = \alpha I_j(t) = 3.5 \times I_j(t), j=x,y,z \quad (5)$$

It should be noted that the identified time delay includes two parts: the time delay caused by system electronics; and the time delay introduced by the modeling method. In some embodiments, a compensator is designed to compensate for the lumped modeling error between the identified model (Eq. (4)) and the real system.

To design and form a digital control system, the discrete-time system model is deduced, which may have the following form:

$$\begin{cases} X_j(k+1) = A_{jd} X_j(k) + B_{jd} u_j(k - D_j) \\ b_j(k) = \alpha I_j(k) = \alpha C_j X_j(k) + \alpha D_j u_j(k - D_j) \end{cases} \quad (6)$$

with initial conditions $$X_j(0) = 0_{p \times 1}, I(0) = 0$$

$$u_j(k-D_j) = 0, \text{ for } k-D<0. \quad (7)$$

In Eq. (6) and (7), k denotes the discretized time and $0_{p \times 1}$ is the zero matrix with a dimension of p×1. If the continuous system is sampled with an interval $T_s$, the discretized time delay $D_j$ equals the integer nearest to $L_j/T_s$, and the system matrices $A_{jd}$ and $B_{jd}$ in Eq. (6) are obtained by zero-order hold (ZOH) method which provides the exact matching between the continuous-time system and discrete-time system at sampling instants for staircase inputs. For the ZOH discretization, system matrices may be obtained by:

$$A_{jd} = e^{A_j T_s},$$

$$B_{jd} = (\int_0^{T_s} e^{A_j t} dt) B_j. \quad (8)$$

In some embodiments, a method for controlling electromagnetic coil system to generate dynamic magnetic fields is based on the unified discrete-time system model, i.e. Eqs. (6) and (7). The method includes: generating control signals for an ECS (e.g., ECS-I or ECS-II); and detecting feedback signals from the ECS; wherein the step of generating control signals comprises: generating the control signals by utilizing linear quadratic integral (LQI) control into a dynamic model for the ECS based on reference signals corresponding to the desired dynamic magnetic fields and the feedback signals, wherein the dynamic model describes open-loop dynamics of the ECS and has a unified state-space form with time delay (as shown in Eqs. (6) and (7)).

Figure 6:
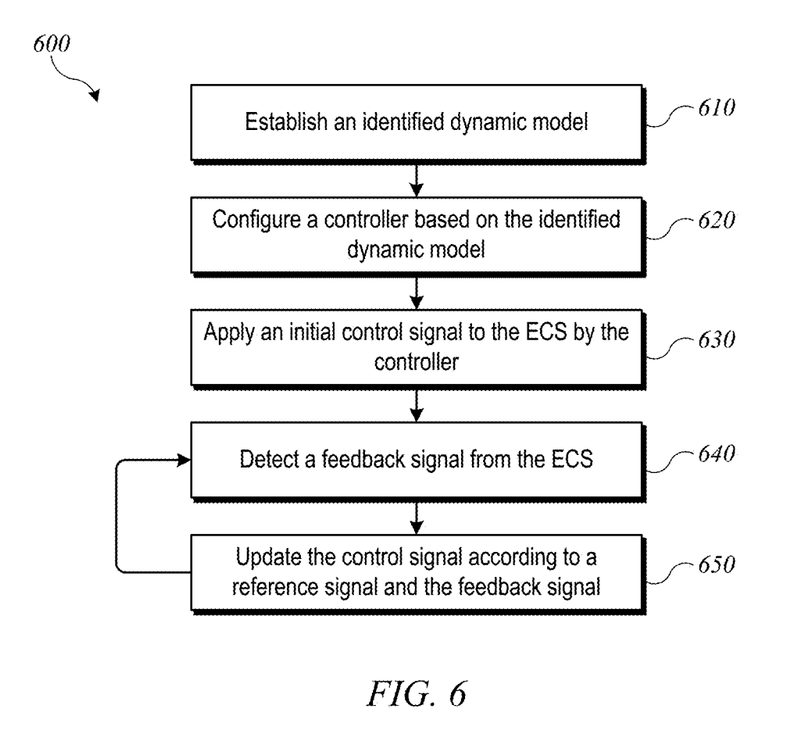
FIG. 6 shows a flowchart of a method for controlling an ECS to generate dynamic magnetic fields according to an embodiment.

FIG. 6 shows a flowchart of a method 600 for controlling an electromagnetic coil system (ECS) to generate dynamic magnetic fields according to an embodiment. Method 600 can be implemented, e.g., in controller 103 of FIG. 1 to control ECS 110. Method 600 starts at block 610, at which a dynamic model is established. The dynamic model describes open-loop dynamics of ECS 110 (as shown in FIG. 1) and has an unified state-space form with time delay. In some embodiments, the dynamic model can be obtained by fitting a p-dimensional minimum-phase state-space model to the experimental frequency response data of electric current and identifying the fitted model by an experimental open-loop step response in time domain. At block 620, a controller 103 is configured based on a dynamic model by integral action control (LQI) technique. At block 630, controller 103 applies an initial control signal to ECS 110. For example, the control signal can be applied to coil driving module(s) 102, which drive current(s) in coil(s) 101 in response to the control signal. At block 640, one or more feedback signals, which are generated in response to the control signal, are detected from the ECS 110. For example, detectors 104 can detect electromagnetic field conditions such as current or magnetic field properties and can generate feedback signals to controller 103. At block 650, controller 103 updates the control signal for controlling ECS 110 based on a reference signal corresponding to a desired dynamic magnetic field of the ECS 200, the one or more detected feedback signals, and one or more system states. Controller 103 may apply the updated control signal to ECS 110, and block 640 may be performed again to detect the feedback signals in response to the updated control signal. Method 600 can continue indefinitely to update the control signal, detect a feedback signal, and update the control signal again.

Figure 7:
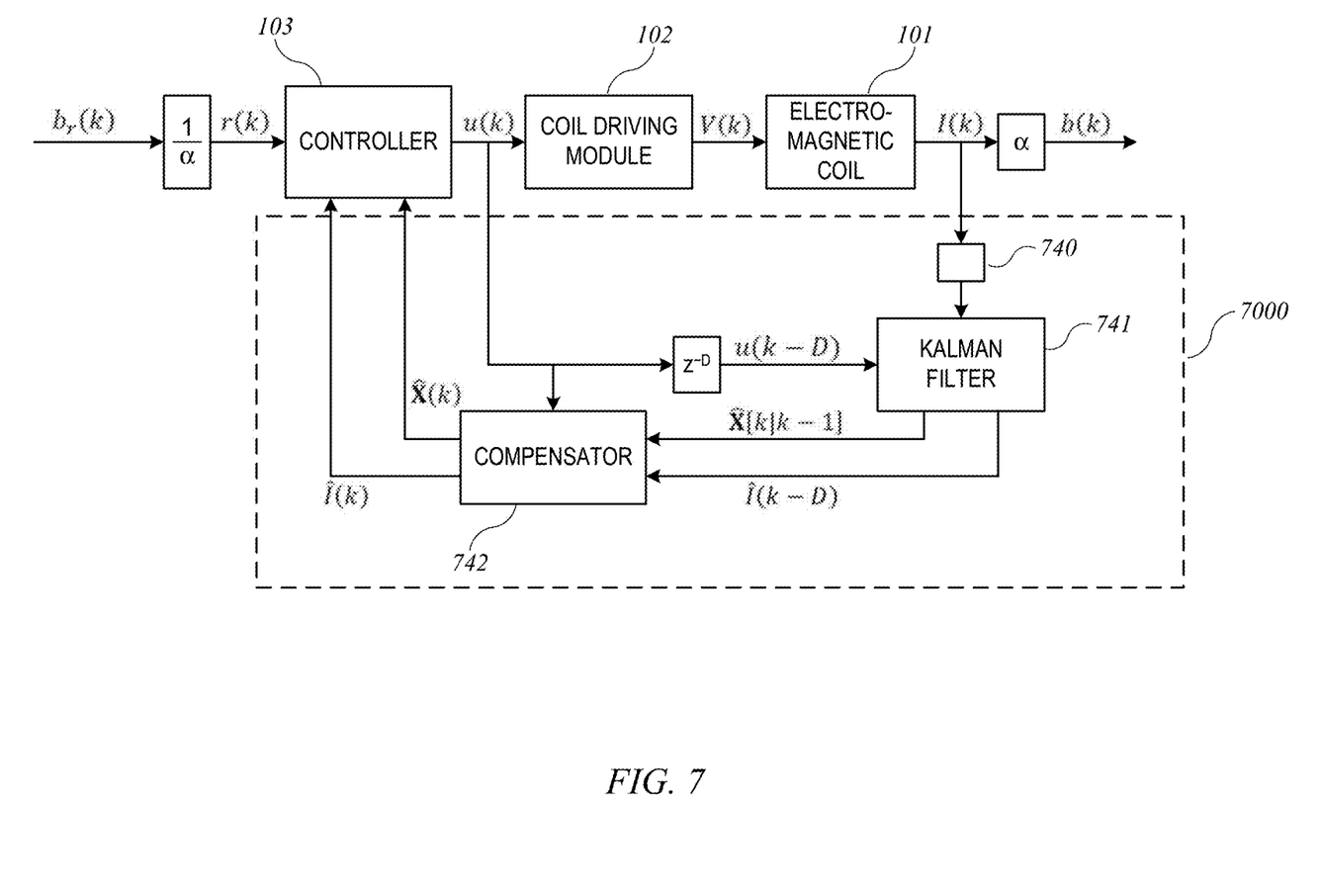
FIG. 7 shows a schematic of a control framework for electromagnetic coil systems according to an embodiment.

FIG. 7 shows an example of a control framework 700 according to an embodiment. Control framework 700 can be implemented, e.g., in detector(s) 104 of control apparatus 100 of FIG. 1. Control framework 700 is shown for one coil (or one axis); those skilled in the art will appreciate that a similar framework can be provided for other coils (or axes) that have the same model form (e.g., Eqs. (4) and (6)). In this example, control framework 700 includes an electric current sensor 740, a Kalman filter 741, and a compensator 742. Electric current sensor 740 measures a feedback signal (such as coil current) in real time. The measured feedback signal may contain noise and may have a time delay. Kalman filter 741 can estimate a noise-free feedback signal. For example, Kalman filter 741 can estimate a noise-free past feedback signal according to the measured feedback signal and a corresponding stored control signal. Kalman filter 741 can also estimate a noise-free past system state according to the measured feedback signal and the corresponding stored control signal. Thus, Kalman filter 741 can correct various errors, such as random error from background and electronics, and/or systematic error due to electronics or material characteristics. Compensator 742 can output a compensated feedback signal without time delay and noise and a compensated system state without time delay and noise. For example, compensator 742 can predict a present system state, a past system state, a present feedback signal and a past feedback signal. The predicting may be implemented using a Smith Predictor based on the identified model. In some embodiments, compensator 742 can also compensate the predicted present system state based on the difference between the predicted past system state and the estimated noise-free past system state (i.e. the system state output from Kalman filter 741) and can compensate the predicted present feedback signal based on the difference between the predicted past feedback signal and the estimated noise-free past feedback signal (i.e. the filtered feedback signal from Kalman filter 741). The compensated predicted present system state and the compensated predicted present feedback signal, which are noise-free and without time-delay, are outputted to controller 103 to update the control signal.

In some embodiments, controller 103 can make the output magnetic field converge to the reference without steady-state error and can optimize the transient response concerning overshoot and settling time. Controller 103 does not require complex control algorithms, which are undesirable in a system that has fast dynamics such that the control system cannot afford heavy computation load in each control interval. For example, controller 103 can utilize the linear quadratic with integral action control (LQI) technique. LQI is a combination of a full-state feedback law, i.e. linear quadratic regulator (LQR) that provides an intrinsically stable closed-loop system with wide phase margin (>60°), and an additional integral action of the feedback. The design process of the discrete-time controller based on LQI is described as follows.

Considering the system model (e.g., Eq. (6)) without time delay, a new state variable $x_i(k)$ related to the integral action of the error of the generated magnetic field may be defined:

$$x_i(k) = x_i(k-1) + r(k) - I(k) = x_i(k-1) + r(k) - CX(k) - Du(k) \quad (9)$$

where $r(k)$ is the vector of corresponding reference, which depends on the feedback type. Thus, the augmented system model may be obtained as:

$$\begin{bmatrix} X(k+1) \\ x_i(k) \end{bmatrix} = \begin{bmatrix} A_d & 0 \\ -C & 1 \end{bmatrix} \begin{bmatrix} X(k) \\ x_i(k-1) \end{bmatrix} + \begin{bmatrix} B_d \\ -D \end{bmatrix} u(k) + \begin{bmatrix} 0 \\ 1 \end{bmatrix} r(k) \quad (10)$$

where 0 is a zero matrix with a suitable size. In order to track dynamic inputs, difference between the reference and output magnetic field should be driven to zero within desirable settling time. To meet this goal, a new augmented system with error vector as the state variables is derived. Let the difference between state variables $\Delta X(k)$ and difference between the integral action $\Delta x_i(k)$ in two consecutive sampling periods be the new state variables and difference of input $\Delta u(k)$ be the new input, which may be defined as:

$$\begin{cases} \Delta X(k) = X(k) - X(k-1) \\ \Delta x_i(k) = x_i(k) - x_i(k-1) \\ \Delta u(k) = u(k) - u(k-1) \end{cases} \quad (11)$$

From Eq. (9), (10) and (11), the new augmented model may be obtained as:

$$\underbrace{\begin{bmatrix} \Delta X(k+1) \\ \Delta x_i(k) \end{bmatrix}}_{\overline{X}(k+1)} = \underbrace{\begin{bmatrix} A_d & 0 \\ -C & 1 \end{bmatrix}}_{\overline{A}} \underbrace{\begin{bmatrix} \Delta X(k) \\ \Delta x_i(k-1) \end{bmatrix}}_{\overline{X}(k)} + \underbrace{\begin{bmatrix} B_d \\ -D \end{bmatrix}}_{\overline{B}} \underbrace{\Delta u(k)}_{\overline{u}(k)} \quad (12)$$

In Eq. (12), the reference $r(k)$ disappears because it is assumed to be an initial step, and $\overline{X}(k)$ and $\overline{u}(k)$ will tend to zero under the stable condition, thereby providing the desired behavior of tracking without steady-state error.

For Eq. (12), LQI can minimize the following cost function:

$$J = \sum_{k=1}^{\infty} \overline{X}^T(k) Q \overline{X}(k) + \gamma \overline{u}^2(k) \quad (13)$$

where $Q \in R^{(p+1) \times (p+1)}$ is a symmetric, positive definite weighting matrix for penalizing the augmented system states and $\gamma$ is the weighting parameter for penalizing the control effort. Different definitions of Q and $\gamma$ lead to different closed-loop behaviors.

In some embodiments, it is desirable to make the output magnetic field converge to the reference as soon as possible, and as long as the load range is well below the rating of ECS, the system dynamics need be not penalized. To this end, only the integral action $\Delta x_i(k)$ among the augmented states is penalized. It can be obtained from Eqs. (9), (11), (12) and (13) that the difference between $r(k)$ and $I(k)$ will decrease to zero with minimum integration, i.e. the transient response is optimized, under suitable penalization of the control effort. Therefore, Q and $\gamma$ may be set to be:

$$Q = \begin{bmatrix} 0_{p \times p} & 0_{p \times 1} \\ 0_{1 \times p} & 1 \end{bmatrix}, \gamma = \gamma_j, j = x, y, z \quad (14)$$

where $\gamma_j$ indicates the penalizing weight of control effort in the cost function, i.e. higher values of $\gamma_j$ result in less requirement of control effort. Since the control effort to reach suitable dynamic performance is specific to a coil axis and since different systems have different actuation capability, $\gamma_j$ (the only parameter) should be adjusted for each coil axis. With only one adjustable parameter for each coil axis, the controller can easily be adapted to different electromagnetic coil systems.

Since the controllability matrix of Eq. (12) has full rank, all the system states are controllable. Therefore, this LQR problem may have the following equivalent optimal control law:

$$\begin{cases} u(k) = K_i x_i(k) - KX(k) \\ [K - K_i] = (\overline{B}^T S \overline{B} + \gamma)^{-1} \overline{B}^T S \overline{A} \end{cases}, \quad (15)$$

where $S \in R^{(p+1) \times (p+1)}$ may be the infinite horizon solution of the associated discrete-time Riccati equation:

$$\overline{A}^T S \overline{A} - S - \overline{A}^T S \overline{B} (\overline{B}^T S \overline{B} + \gamma)^{-1} \overline{B}^T S \overline{A} + Q = 0. \quad (16)$$

As noted above, some embodiments may use a Kalman filter (e.g., Kalman filter 741 of FIG. 7) to estimate a noise-free feedback signal. In some embodiments, the only measured variable in the ECSs is the time-delayed coil current. Where system process and/or current measurement noise is present, feeding back the current signal directly is sub-optimal; the Kalman filter can be used as described with reference to FIG. 7 to estimate the system states and denoised time-delayed coil current.

For the aforementioned estimation purpose, a Kalman filter can be employed as an estimator in the control framework shown in FIG. 7. It is assumed that $w(k) \in R^{p \times 1}$ and $v(k)$ are independently distributed Gaussian white process noise vector and current measurement noise, respectively. Their covariance matrices may be defined by:

$$\varepsilon\{W(k) w^T(k)\} = R_w \text{ and}$$

$$\varepsilon\{v(k) w^T(k)\} = R_v, \quad (17)$$

which are obtained by experimental data.

The developed steady-state discrete-time Kalman filter may have the following form:

$$\begin{cases} \hat{X}[k+1|k] = A_d\hat{X}[k|k-1] + B_du(k-D) + \\ \quad \kappa\big(I(k) - C\hat{X}[k|k-1] - Du(k-D)\big) \\ \hat{b}(k-D) = \alpha\hat{I}(k-D) = \alpha C\hat{X}[k|k-1] + \alpha Du(k-D) \end{cases} \quad (18)$$

With zero initial conditions, in Eq. (18), $\hat{X}[k+1|k]$ and $\hat{X}[k|k-1]$ are the estimates of $X(k+1)$ and $X(k)$ based on the past system information, respectively; $\hat{b}(k-D)$ is the estimate of time-delayed magnetic field strength; $\kappa \in R^{p \times 1}$ is the steady-state Kalman filter gain obtained by:

$$\kappa = pC^T R_v^{-1} \quad (19)$$

where $P \in R^{p \times p}$ is the solution of the following algebraic Riccati equation:

$$0 = PA_d^T + A_d P + R_w - PC^T R_v^{-1} CP \quad (20)$$

Figure 8:
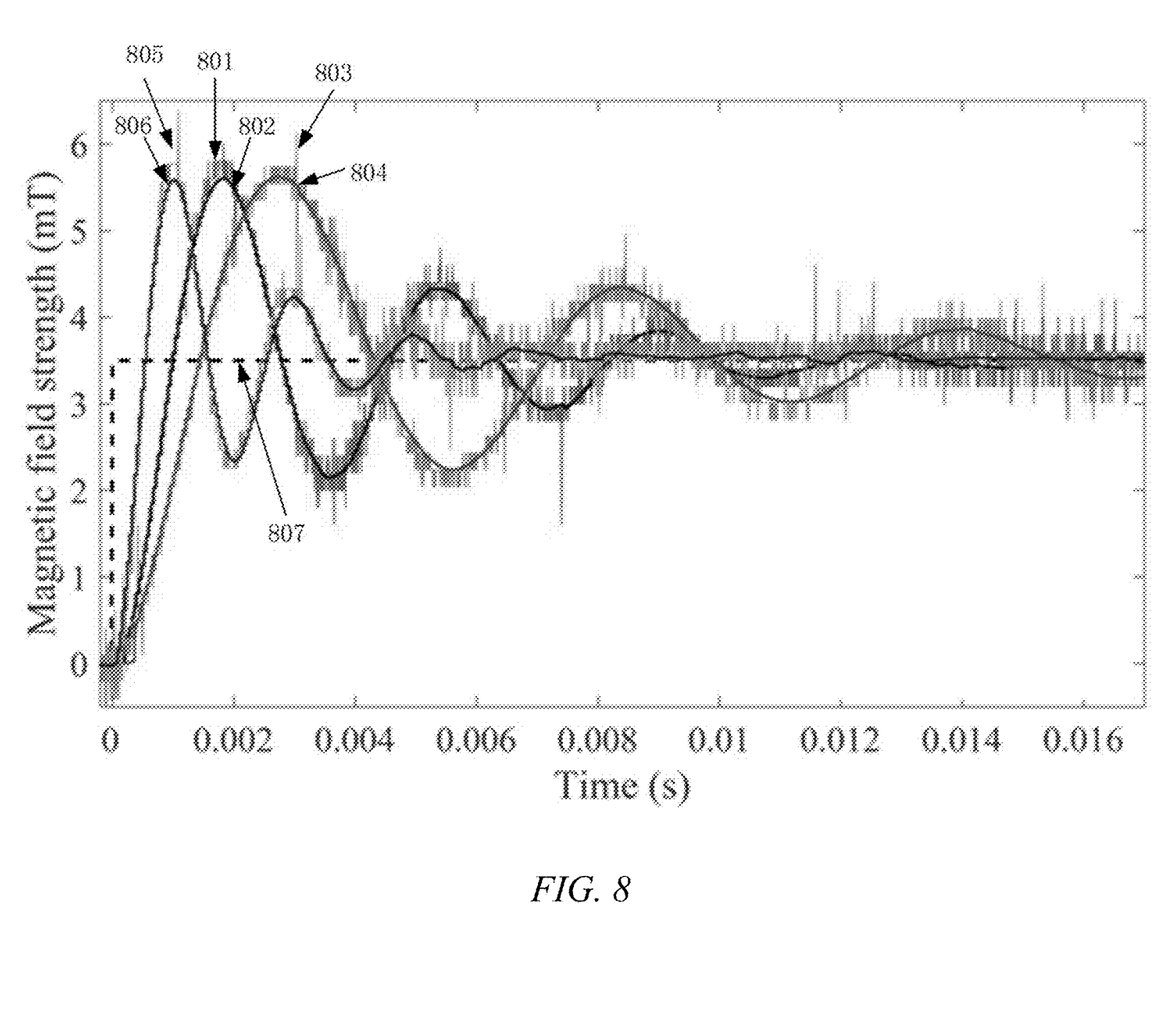
FIG. 8 shows a validation of the Kalman filter using experimental data of open-loop step responses of ECS-I according to an embodiment.

The developed Kalman filter has been validated using the experimental data of open-loop step response of ECS-I after calibrating $R_w$ and $R_v$. A simulation result (sampling time: 40 μs) for the validation of the Kalman filter using experimental data of open-loop step responses of ECS-I is shown in FIG. 8. Curve 801 represents experimental data of X axis, curve 802 represents the data of Kalman filter on X axis, curve 803 represents experimental data of Y axis, curve 804 represents the data of Kalman filter on Y axis, curve 805 represents the experimental data of Z axis, curve 806 represents the data of Kalman filter on Z axis, and dotted line 807 represents the reference. From FIG. 8 it can be seen that the Kalman filter can estimate the time-delayed coil currents precisely.

The Kalman filter as described can estimate a noise-free feedback signal and to estimate the system state. However, the output of the Kalman filter is time delayed. The time delay should be considered for applying the control to the ECSs in order to avoid large overshoot or instability in the closed-loop system. Accordingly, some embodiments may also use a compensator (e.g., compensator 742 of FIG. 7) to compensate for time delay.

In some embodiments, compensator 742 uses a design inspired by the Smith predictor to compensate for the time delay and the lumped modeling error. The Smith predictor may be described by:

$$\begin{cases} X_p(k+1) = A_d X_p(k) + B_d u(k) \\ I_p(k) = C X_p(k) + Du(k) \end{cases} \quad (21)$$

$$\begin{cases} X_{pd}(k+1) = A_d X_{pd}(k) + B_d u(k-D) \\ I_{pd}(k) = C X_{pd}(k) + Du(k-D) \end{cases} \quad (22)$$

With zero initial conditions, in Eq. (21) and (22), $I_p(k)$ and $X_p(k)$ are the predictions of coil current and system states without time delay respectively, and $I_{pd}(k)$ and $X_{pd}(k)$ are the predicted time-delayed coil current and system states. For purpose of time delay and modeling error compensation, the delay-free feedback of coil current and system states may be corrected in the compensator as:

$$\begin{cases} \hat{I}(k) = I_p(k) + \hat{I}(k-D) - I_{pd}(k) \\ \hat{X}(k) = X_p(k) + \hat{X}[k|k-1] - X_{pd}(k) \end{cases} \quad (23)$$

Simulations have been conducted to evaluate the dynamic performances of the often used open-loop control for ECS I and PI control for ECS II and to evaluate the parameter tuning process of a controller as described above and the effectiveness of the control framework on the two systems.

The discretized system model (Eq. (6)) with calibrated noise was employed for simulation. A discrete-time control framework as described with reference to FIG. 7 was implemented in the control systems of ECS-I and ECS-II. After testing the computation capabilities of the two ECSs and to meet the Shannon theorem, the sampling time was set. System dynamic performances were evaluated based on step response because any discrete-time process is composed of step responses and any continuous signal can be approximated by a finite number of discrete steps.

One simulation modeled ECS-I with conventional open-loop control. Simulation results of open-loop step responses of ECS-I are shown in FIG. 4, from which it can be obtained that the maximum overshoot and settling time are, for example, about 60% and 17 ms, respectively. Thus, conventional open-loop control systems would provide poor dynamic tracking performance for magnetic fields with frequencies above 40 Hz. In addition, oscillations with large amplitudes can be damaging to the system and should be avoided in real applications in order to increase the system life span.

A second simulation modeled ECS-II with conventional PI control. The PI controllers for the three axes were tuned using the MATLAB PID tuning algorithm, and the gain values (PG=Proportional gain and IG=integral gain) were determined as follows: $PG_x$=7.265, $IG_x$=0.4206, $PG_y$=4.45, $IG_y$=0.0886, $PG_z$=6.4158 and $IG_z$=0.3965. From the simulation results of dynamic magnetic field strengths during the step responses of ECS-II with PI control (control frequency: 62.5 kHz), it can be obtained that the maximum overshoot and settling time are around 45% and 7 ms, respectively. Thus, conventional PI control performance is not satisfactory for dynamic magnetic fields with frequencies beyond 70 Hz. Also, the noise in feedback causes oscillation in control inputs and this leads to system chattering, which can be observed in experimental results.

Additional simulations were conducted to evaluate a control system according to an embodiment described herein. Simulations were used to determine suitable parameters (Eq.(15)) of the controller for different coil axes. The tuning process was accomplished simply by assigning different values of γ (Eq.(14)). Taking the X axis as an example, the controller parameter tuning can be based on the step response, with $\gamma_x$ chosen via trial and error. It can be seen from the simulation results for ECS-I and ECS-II that higher value of yx leads to lower required control effort. Meanwhile, the two systems both have similar transient responses: the maximum overshoots are around 3%, and the settling times are significantly suppressed compared with conventional open-loop control (for ECS-I) and PI control (for ECS-II). In addition, the noise in control inputs of the control framework can be eliminated (or greatly reduced) by the Kalman filter. The easy parameter tuning process introduced above shows that, for specific systems with different coils and coil driving modules, one can apply the control framework simply by tuning the value of γ, which makes the control system convenient to implement across different ECSs.

System chattering can be clearly observed for the system with PI control due to the feedback noise. On the contrary, control inputs in control frameworks according to embodiments described herein are very smooth so that system chattering is avoided. Also, the dynamic transient performances and required control efforts in the experiments for ECS-II are consistent with the simulations, although there is modeling error in the identified system model.

The experimental results of step responses for the two example ECSs show that a discrete-time control framework according to some embodiments of the present invention can significantly improve the transient performances of typical ECSs and is robust to the modeling error. Furthermore, the control framework can enable a typical ECS to generate high-frequency dynamic magnetic fields accurately.

In this disclosure, a discrete-time control framework is presented that allows generation of high-accuracy dynamic magnetic fields, e.g., for actuation of magnetic microrobots. With the unified state-space models, the discrete-time controller is designed based on the LQI technique which ensures the systems with optimal transient response and accurate tracking features. Noise, state estimation, and modeling error can be addressed by the Kalman filter and compensator (inspired by the Smith predictor). The control framework has low computational demand, which allows it to be implemented inexpensively in real-time systems with high control frequencies (for example, 25 kHz for ECS-I and 62.5 kHz for ECS-II). Some embodiments provide significantly improved dynamic performance compared with the open-loop system for ECS-I and PI control for ECS-II in terms of the overshoot and settling time. In addition, system chattering in the PI control can be effectively eliminated. Furthermore, experiments of tracking of a 3D rotating magnetic field demonstrate that conventional control methods cannot generate high-frequency dynamic magnetic fields accurately, while a control framework of the kind described herein can significantly improve the tracking performance for the ECSs. Control frameworks of the kind described herein can be applied to different digitally controlled ECSs simply by tuning its parameters.

In some embodiments, the controller, Kalman filter, compensator, and other components described herein may be implemented using computer systems. Such systems may comprise a processor (e.g., a microprocessor, microcontroller, application-specific integrated circuit (ASIC), field-programmable gate array (FPGA), or the like); a memory for storing data and/or program code to be executed by the processor; a permanent storage unit, such as a disk drive; a communications port for handling communications with external devices; and user interface devices, including a touch panel, keys, buttons, displays, speakers, etc. When software modules or algorithms are involved, these software modules may be stored on a computer-readable storage medium as program instructions or computer readable codes executable on a processor. Examples of computer readable storage media include semiconductor-based storage media (e.g., read-only memory (ROM), random-access memory (RAM), flash memory), magnetic storage media (e.g., floppy disks, hard disks, etc.), and optical recording media (e.g., CD-ROMs, or Digital Versatile Discs (DVDs)). In some embodiments, program instructions or computer readable codes can also be distributed over network coupled computer systems so that the computer readable code is stored and executed in a distributed manner.

Control apparatus and methods according to embodiments described herein can be used in any system where it is desirable to generate dynamic electromagnetic fields with precise control, particular at high operating frequencies. Examples of such systems include (but are not limited to) control systems for microrobots, imaging systems for magnetic particle measurement, and control systems for transcranial magnetic stimulation (TMS) systems.

In addition, control apparatus and methods according to embodiments described herein can be used with other types of electromagnetic field generating system, not limited to ECS systems as described above. For example, another type of electromagnetic field generating system may use a set of magnets (which can be electromagnets or permanent magnets) and a set of mechanical actuators to adjust the positions of the magnets, thereby providing a dynamic magnetic field. In such cases, coil(s) 101 of FIG. 1 can be replaced by one or more magnets and coil driving module(s) 102 can be replaced by one or more mechanical actuators operable to adjust the positions (including spatial location and/or orientation) of the one or more magnets in response to control signals. Controller 103 can use a dynamic model of the kind described above to determine a desired position or physical arrangement for the magnet(s) and generate corresponding control signals to the mechanical actuator(s). In embodiments where at least one of the magnets is an electromagnet (or otherwise capable of varying the strength of its magnetic field), controller 103 can also determine a driving current (or other parameter controlling magnetic strength) for the electromagnet.

While the invention has been described with reference to specific embodiments, those skilled in the art will appreciate that variations and modifications are possible. All processes described above are illustrative and may be modified. Processing operations described as separate blocks may be combined, order of operations can be modified to the extent logic permits, processing operations described above can be altered or omitted, and additional processing operations not specifically described may be added. Particular definitions and data formats can be modified as desired. Similarly, functional blocks may be realized by any number of hardware and/or software components configured to perform the specified functions. For example, exemplary embodiments may employ various integrated circuit (IC) components, e.g., memory elements, processing elements, logic elements, look-up tables, and the like, which may carry out a variety of functions under the control of one or more microprocessors or other control devices. Similarly, where the elements are implemented using software programming or software elements, the embodiments described herein may be implemented with any programming or scripting language such as C, C++, Java, assembler language, or the like, with the various algorithms being implemented with any combination of data structures, objects, processes, routines or other programming elements. Operations described herein may be implemented in algorithms that are executed on one or more processors. Furthermore, the exemplary embodiments described herein may employ any number of conventional techniques for electronics configuration, signal processing and/or control, data processing and the like.

Thus, although the invention has been described with respect to specific embodiments, it will be appreciated that the invention is intended to cover all modifications and equivalents within the scope of the following claims.

What is claimed is:

1. A method for controlling an electromagnetic field generation system to generate dynamic magnetic fields, the method comprising:
   establishing a dynamic model describing open-loop dynamics of the electromagnetic field generation system, the dynamic model having an unified state-space form with time delay;
   configuring a controller based on the dynamic model;

applying, by the controller, a control signal to the electromagnetic field generation system;

detecting, by the controller, one or more feedback signals from the electromagnetic field generation system, wherein the one or more feedback signals are generated by a detector in response to the control signal and an electromagnetic field condition; and updating, by the controller, the control signal for controlling the electromagnetic field generation system, based in part on a reference signal corresponding to a desired dynamic magnetic field of the electromagnetic field generation system and in part on the one or more detected feedback signals and one or more system states of the electromagnetic field generation system.

2. The method according to claim 1, wherein establishing the dynamic model includes:

fitting a p-dimensional minimum-phase state-space model with open-loop frequency response data of sensor feedback of the electromagnetic field generation system; and identifying a fitted model based on an open-loop step response in time domain of the electromagnetic field generation system, wherein the identified fitted model is established as the dynamic model.

3. The method according to claim 2, wherein configuring the controller further includes:

configuring the controller based on the identified fitted model by a linear quadratic with integral action (LQI) technique.

4. The method according to claim 3, wherein configuring the controller further includes:

delivering control inputs to the electromagnetic field generation system to generate open-loop dynamic electromagnetic fields; and obtaining the open-loop frequency response data and the open-loop step response based on the generated electromagnetic fields and the control inputs.

5. The method according to claim 2, wherein establishing the dynamic model further includes:

transforming the identified fitted model from a continuous-time system model into a discrete-time system model, wherein the transformed model is established as the dynamic model.

6. The method according to claim 5, wherein configuring the controller includes:

adding an integral action augmented state into the dynamic model to form an augmented system model to minimize tracking error during control, wherein the integral action augmented state describes an integral action of an error of the magnetic field generated by a connected load; and configuring the controller based on the augmented system model.

7. The method according to claim 6, wherein configuring the controller based on the augmented system model includes:

providing the augmented system model with an adjustable control weighting parameter for penalizing a control effort;

adjusting a value of the control weighting parameter based on an actuation capability of the electromagnetic field generation system; and using the adjusted control weighting parameter in configuring the controller.

8. The method according to claim 1, wherein the electromagnetic field generation system is a multi-axis system having one pair of load driving module and connected load for each axis and wherein establishing the dynamic model includes:

fitting a p-dimensional minimum-phase state-space model with open-loop frequency response data of electrical current for each axis of the electromagnetic field generation system; and identifying a fitted model for each axis of the electromagnetic field generation system based on an open-loop step response in time domain of each axis of the electromagnetic field generation system, wherein the identified fitted model for each axis of the electromagnetic field generation system is taken as the dynamic model of that axis of the electromagnetic field generation system.

9. The method according to claim 8, wherein configuring the controller includes:

adding an integral action augmented state into the dynamic model to form an augmented system model to minimize tracking error during control, wherein the integral action augmented state describes an integral action of an error of the magnetic field generated by a connected load;

providing the augmented system model with a weighting matrix for penalizing states of the augmented system model and a control weighting parameter for penalizing a control effort;

adjusting a value of the weighting matrix and the control weighting parameter for each axis of the electromagnetic field generation system; and using the weighting matrix and the control weighting parameter in configuring the controller.

10. The method according to claim 1, wherein generating the one or more feedback signals by the detector includes:

storing the control signal in real time;

measuring a feedback signal of the electromagnetic field generation system in real time;

estimating a noise-free past system state and a noise-free past feedback signal based on the measured feedback signal and the stored control signal;

predicting, based on the dynamic model, a present state of the system, a past state of the system, a present feedback signal from the system, and a past feedback signal from the system;

compensating the predicted present state based on a difference between the predicted past state and the estimated noise-free past system state;

compensating the predicted present feedback signal based on a difference between the predicted past feedback signal and the estimated noise-free past feedback signal; and outputting the compensated present state and the compensated present feedback signal to the controller, wherein the compensated present feedback signal is taken as the one or more detected feedback signals, and the compensated present state is taken as the one or more system states.

11. The method according to claim 10, wherein updating the control signal includes:

updating the control signal based on the compensated present feedback signal, the compensated present state and the reference signal corresponding to a desired dynamic magnetic field.

12. The method according to claim 11, wherein the estimating is implemented by a Kalman filter based on experimental open-loop step response data in a time domain.

13. The method according to claim 11, wherein the predicting is implemented by a Smith predictor based on the dynamic model according to the stored control signal in real-time.

14. An apparatus for controlling electromagnetic field generation system to generate dynamic magnetic fields, the apparatus comprising:
a controller configured to apply a control signal to the electromagnetic field generation system; and
a detector configured to measure one or more electromagnetic field conditions from the electromagnetic field generation system and to generate one or more feedback signals to the controller, wherein the one or more feedback signals are generated in response to the control signal and the one or more electromagnetic field conditions,
wherein the controller is further configured to update the control signal based in part on a reference signal corresponding to a desired dynamic magnetic field of the electromagnetic field generation system and based in part on the one or more feedback signals and one or more system states; and
wherein the controller is further configured to update the control signal based on a dynamic model for describing open-loop dynamics of the electromagnetic field generation system that has an unified state-space form with time delay.

15. The apparatus according to claim 14, wherein the electromagnetic field generation system comprises a load driving module and a connected load.

16. The apparatus according to claim 15, wherein the connected load comprises one or more wire sections connected in series or parallel.

17. The apparatus according to claim 15, wherein the electromagnetic field generation system is an electromagnetic coil system (ECS), wherein the load driving module is a coil driving module and the load is a coil connected to the coil driving module.

18. The apparatus according to claim 14, wherein the electromagnetic field generation system is a multi-axis system and comprises a load driving module and a connected load for each axis.

19. The apparatus according to claim 14, wherein the electromagnetic field generation system comprises a set of one or more magnets and at least one mechanical actuator operable to adjust a position of at least one of the magnets.

20. The apparatus according to claim 14, wherein the apparatus further comprises:
a model unit configured to fit a p-dimensional minimum-phase state-space model with open-loop frequency response data of sensor feedback of the electromagnetic field generation system and to identify the fitted model by an experimental open-loop step response in time domain of the electromagnetic field generation system, wherein the identified model is established as the dynamic model.

21. The apparatus according to claim 20, wherein the controller is configured based on the identified model by a linear quadratic with integral action (LQI) technique.

22. The apparatus according to claim 20, wherein the detector comprises:
a storing unit configured to store the control signal in real-time;
a measuring unit configured to measure a feedback signal of the electromagnetic field generation system in real-time;
an estimating unit configured to estimate a noise-free past system state and a noise-free past feedback signal based on the measured feedback signal and the stored control signal;
a predicting unit configured to predict, based on the dynamic model, a present state of the system, a past state of the system, a present feedback signal from the system, and a past feedback signal from the system;
a compensating unit configured to compensate the predicted present state based on a difference between the predicted past state and the estimated noise-free past system state and to compensate the predicted present feedback signal based on a difference between the predicted past feedback signal and the estimated noise-free past feedback signal; and
an outputting unit configured to output the compensated present state and the compensated present feedback signal to the controller, wherein the compensated present feedback signal is taken as the measured feedback signal, and the compensated present state is taken as the one or more system states.

23. The apparatus according to claim 22, wherein the controller is further configured to update the control signal based on the compensated present feedback signal, the compensated present state and the reference signal.

24. The apparatus according to claim 22, wherein the measured feedback signal is an electric current signal.

25. The apparatus according to claim 22, wherein the measured feedback signal is a magnetic flux density signal.

26. The apparatus according to claim 20, wherein the model unit provides a weighting matrix for penalizing states of an augmented system model that is formed by adding an integral action augmented state into the state-space model; and the weighting matrix is adjustable to adopt different properties in the electromagnetic field generation system.

27. The apparatus according to claim 20, wherein the model unit provides a control weighting parameter for penalizing a control effort, and the control weighting parameter is adjustable to allow different actuation capability of the electromagnetic field generation system.

28. The apparatus according to claim 20, wherein the electromagnetic field generation system is a multi-axis system and comprises one pair of load driving module and connected load for each axis; and the model unit provides a weighting matrix for penalizing states of an augmented system model, which is formed by adding an integral action augmented state into the state-space model; and the weighting matrix is adjustable for each axis to adopt different properties in each axis of the electromagnetic field generation system.

29. The apparatus according to claim 20, wherein the electromagnetic field generation system is a multi-axis system and comprises one pair of load driving module and connected load for each axis; and the model unit provides a control weighting parameter for penalizing a control effort, and the control weighting parameter is adjustable for each axis of the electromagnetic field generation system.

* * * * *